United States Patent [19]

Aschwanden et al.

[11] 4,452,807
[45] Jun. 5, 1984

[54] (R,S)-1-(3-HYDROXY-4-METHOXYBEN-ZOYL)-3-HYDROXY-2-PYRROLIDINONE INTERMEDIATES THEREFOR AND USE FOR TREATING CEREBRAL INSUFFICIENCY

[75] Inventors: Werner Aschwanden, Ettingen; Emilio Kyburz, Reinach, both of Switzerland

[73] Assignee: Hoffmann-La Roche Inc., Nutley, N.J.

[21] Appl. No.: 340,920

[22] Filed: Jan. 20, 1982

[30] Foreign Application Priority Data

Feb. 5, 1981 [CH] Switzerland ........................ 770/81

[51] Int. Cl.³ .................... A61K 31/40; C07D 207/12
[52] U.S. Cl. ................................. 424/274; 548/544; 548/110
[58] Field of Search ................ 548/544, 110; 424/274

[56] References Cited

U.S. PATENT DOCUMENTS 4,239,770 12/1980 Kyburz et al. ...................... 424/274

FOREIGN PATENT DOCUMENTS 845099 2/1977 Belgium .

OTHER PUBLICATIONS

Yakhontov et al., Chem. Abstr. vol. 86 (1977), 5393r.

Primary Examiner—Paul M. Coughlan, Jr.
Assistant Examiner—D. B. Springer
Attorney, Agent, or Firm—Jon S. Saxe; Bernard S. Leon; William G. Isgro

[57] ABSTRACT 1-(3-Hydroxy-4-methoxybenzoyl)-3-hydroxy-2-pyrrolidinone of the formula

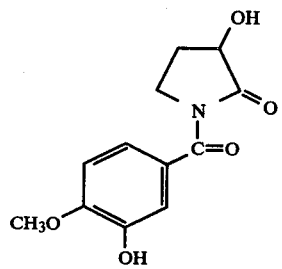

I suitable for the control or prevention of cerebral insufficiency is described. The compound contains an asymmetric carbon atom. Therefore, the two optically active enantiomeric forms as well as the racemate are described. The compound of formula I can be prepared by cleaving the protecting group(s) from a corresponding compound in which at least one of the two hydroxy groups is protected.

7 Claims, No Drawings

(R,S)-1-(3-HYDROXY-4-METHOXYBENZOYL)-3-HYDROXY-2-PYRROLIDINONE INTERMEDIATES THEREFOR AND USE FOR TREATING CEREBRAL INSUFFICIENCY

SUMMARY OF THE INVENTION

The invention relates to 1-(3-Hydroxy-4-methoxybenzoyl)-3-hydroxy-2-pyrrolidinone of the formula

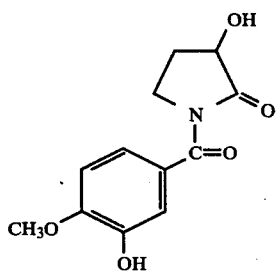

I which is suitable for the control or prevention of cerebral insufficiency. Since this compound contains an asymmetric carbon atom, the two optically active enantiomers as well as the racemate are part of the invention.

In another aspect, the invention relates to intermediates of the formula

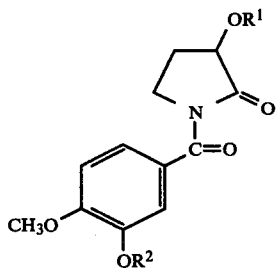

II wherein one of $R^1$ and $R^2$ is a protecting group and the other is hydrogen or a protecting group.

In yet another aspect, the invention relates to pharmaceutical composiions containing the compound of formula I and the method of using such compositions in the control or prevention of cerebral insufficiency.

DETAILED DESCRIPTION OF THE INVENTION

The invention relates to a pyrrolidine derivative. More particularly, the invention relates to 1-(3-hydroxy-4-methoxybenzoyl)-3-hydroxy-2-pyrrolidinone of the formula

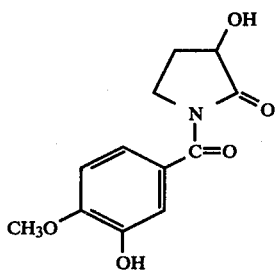

I

The compound possesses valuable pharmacodynamic properties.

Objects of the present invention are 1-(3-hydroxy-4-methoxybenzoyl)-2-pyrrolidinone of formula I, the preparation of this compound and intermediates for the preparation of this compound, pharmaceutical compositions containing the compound of formula I as well as the use of the compound of formula I in the control or prevention of illnesses or in the improvement of health, especially in the control or prevention of cerebral insufficiency.

The compound of formula I contains an asymmetric carbon atom. Therefore, the invention covers not only the optically active enantiomeric forms of the compound of formula I, but also mixtures thereof, especially the racemate.

The pyrrolidine derivative of formula I can be prepared in accordance with the invention by removing the protecting group(s) from a pyrrolidine derivative of the formula

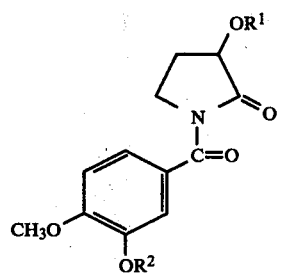

II wherein one of $R^1$ and $R^2$ is a protecting group and the other is hydrogen or a protecting group.

As the protecting groups in the pyrrolidine derivatives of formula II, suitable are only those which can be cleaved by methods in which these protecting groups are selectively removed without affecting other structural elements present in the molecule. The removal of the protecting group(s) from the pyrrolidine derivatives of formula II is carried out according to known methods. However, the nature of the protecting group(s) to be removed must be taken into consideration when choosing the method to be used and care must be taken that only the respective protecting group is selectively removed without affecting other structural elements present in the molecule.

Formula II hereinbefore firstly relates to compounds of the formula

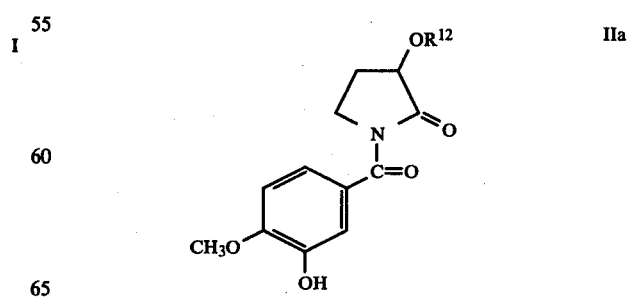

IIa wherein $R^{12}$ is a protecting group,
secondly compounds of the formula

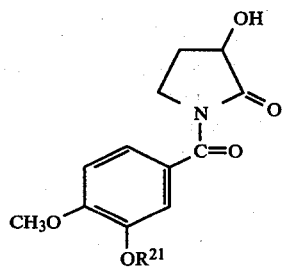

wherein $R^{21}$ is a protecting group,
and thirdly compounds of the formula

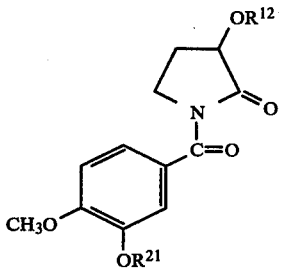

wherein $R^{12}$ and $R^{21}$ each, independently, is a protecting group.

Suitable as protecting groups which are denoted by $R^{12}$ are, for example, readily cleavable alkyl and aralkyl groups, such as, substituted trityl groups, for example, p-methoxytrityl, p,p'-dimethoxytrityl or p,p'p'''-trimethoxytrityl, and the like; readily cleavable metal-organic groups, especially, trialkylsilyl groups, such as, trimethylsilyl, and the like; readily cleavable acetal and ketal protecting groups such as tetrahydropyran-2-yl, 4-methoxytetrahydropyran-4-yl and the like; readily cleavable acyl groups, such as, acetyl, chloroacetyl, trifluoroacetyl, methoxyacetyl, phenoxyacetyl, benzyloxycarbonyl, trichloroethoxycarbonyl, tribromoethoxycarbonyl, benzoylformyl and the like.

Methods for the removal of the groups mentioned earlier as examples of protecting groups denoted by $R^{12}$ as described in the literature and, accordingly, are familiar to any person skilled in the art. For example, the aforementioned mono-, di- and trimethoxytrityl groups can be cleaved by treatment with 80% acetic acid at room temperature, the trimethylsilyl group can be cleaved by treatment with dilute hydrochloric acid in tetrahydrofuran or the like, the tetrahydropyran-2-yl group and the 4-methoxytetrahydropyran-4-yl group can be cleaved under mild acidic conditions, for example, by means of 0.1 normal hydrochloric acid, the acetyl group can be cleaved by means of esterase enzymes, the chloroacetyl group can be cleaved by means of thiourea/pyridine, the trifluoroacetyl group can be cleaved by means of methanol, the methoxyacetyl and the phenoxyacetyl group can be cleaved by means of methanolic ammonia, the benzyloxycarbonyl group can be cleaved by catalytic hydrogenation, for example, over palladium/carbon, the trichloroethoxycarbonyl and the tribromoethoxycarbonyl group can be cleaved by means of zinc/copper in glacial acetic acid at room temperature and the benzoylformyl group can be cleaved by treatment with aqueous pyridine at room temperature.

Suitable as protecting groups which are denoted by $R^{21}$ are, for example, readily cleavable alkyl groups, such as, thert.butyl and the like; readily cleavable aralkyl groups, such as, benzyl and the like; readily cleavable metal-organic groups, especially trialkylsilyl groups, such as, trimethylsilyl and the like; readily cleavable acetal and ketal protecting groups, such as, tetrahydropyran-2-yl and the like; readily cleavable acyl groups such as fluorenecarbonyl, benzyloxycarbonyl, trichloroethoxycarbonyl, tribromoethoxycarbonyl and the like.

Methods for the cleavage of the groups mentioned earlier as examples of protecting groups denoted by $R^{21}$ are described in the literature and, accordingly, are familiar to any person skilled in the art. Thus, for example, the benzyl and the benzyloxycarbonyl group can be cleaved by catalytic hydrogenation, for example, over palladium/carbon, the tert.butyl, the trimethylsilyl and the tetrahydropyran-2-yl group can be cleaved under mild acidic aqueous conditions, the fluorenecarbonyl group can be cleaved by means of UV-light and the trichloroethoxy-carbonyl and the tribromoethoxycarbonyl group can be cleaved by heating in methanol or by means of zinc/copper in glacial acetic acid.

Examples of compounds of formula II are:
1-(3-Hydroxy-4-methoxybenzoyl)-2-oxo-3-pyrrolidinyl-acetate (A),
1-(3-benzyloxy-4-methoxybenzoyl)-3-hydroxy-2-pyrrolidinone (B),
3-(benzyloxycarbonyloxy)-1-(3-benzyloxy-4-methoxybenzoyl)-2-pyrrolidinone (c),
1-(3-benzyloxy-4-methoxybenzoyl)-2-oxo-3-pyrrolidinyltrifluoroacetate (D) and
1-(3-benzyloxy-4-methoxybenzoyl)-2-oxo-3-pyrrolidinylacetate (E).

The compound denoted earlier as A is a compound of formula IIa in which $R^{12}$ is acetyl. This compound can be converted into the compound of formula I hereinbefore by means of esterase enzymes.

The compound denoted earlier as B is a compound of formula IIb in which $R^{21}$ is benzyl. This compound can be converted into the compound of formula I hereinbefore by catalytic hydrogenation, for example, over palladium/carbon.

The compounds denoted earlier as C, D and E are compounds of formula IIc. Compound C is a compound of formula IIc in which $R^{12}$ is benzyloxycarbonyl and $R^{21}$ is benzyl. Compound D is a compound of formula IIc in which $R^{12}$ is trifluoroacetyl and $R^{21}$ is benzyl. Compound E is a compound of formula IIc in which $R^{12}$ is acetyl and $R^{21}$ is benzyl. Compound C is an example of a compound of formula IIc which can be converted into the compound of formula I hereinbefore in one operation with cleavage of both protecting groups. The cleavage can be carried out by catalytic hydrogenation, for example, over palladium/carbon. Compound D is an example of a compound of formula IIc which can be converted into the compound of formula I hereinbefore in two operations; for example, the trifluoroacetyl group can firstly be cleaved by means of methanol to give compound B which then, as already mentioned, can be converted into the compound of formula I by catalytic hydrogenation, for example, over palladium/carbon. Compound E is another example of a compound of formula IIc which can be converted into the compound of formula I hereinbefore in two operations; for example, by cleavage of the benzyl group by catalytic hydrogenation, for example, over palladium/- carbon, there can be obtained compound A which then, as already mentioned, can be converted into the compound of formula I by means of esterase enzymes. Having regard to the nature of the two protecting groups and taking into consideration the methods available for the removal of these protecting groups, it will be readily apparent to a person of ordinary skill in the art whether a particular compound of formula IIc can be converted into the compound of formula I in one operation or in two operations.

The starting materials of formula II hereinbefore are also an object of the invention.

Compounds of formula II in which $R^1$ and $R^2$ each is a protecting group, that is, compounds of formula IIc, can be prepared, for example, by appropriately acylating a pyrrolidine derivative of the formula

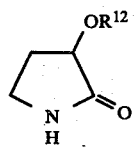

III wherein $R^{12}$ is as previously described, in the 1-position, that is, replacing the hydrogen atom in the 1-position of a compound of formula III by a correspondingly substituted benzoyl group. This can be carried out using methods which are generally known for such acylations. The acylation agent used is a sufficiently reactive derivative of an acid of the formula

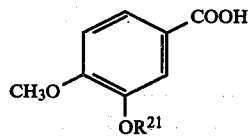

wherein $R^{21}$ is as previously described, especially a reactive imidazolide or halide of this acid, for example, 3-benzyloxy-4-methoxybenzoyl chloride.

The aforementioned acylation is conveniently carried out by firstly treating the compound of formula III with a base capable of removing the hydrogen atom on the nitrogen atom in the 1-position, for example, with butyl lithium, and then reacting with the reactive derivative of the acid of formula IV. It is also possible to use the compound of formula III in the form of a reactive derivative in which a readily cleavable group, especially a trialkylsilyl group, such as, 1-trimethylsilyl, is present on the nitrogen atom in the 1-position; in this case the protecting groups ($R^{12}$) can, of course, only be groups which are not affected under the conditions of the acylation.

The compounds of formula III can, in turn, be prepared, for example, from 3-hydroxy-2-pyrrolidone by introduction of the desired protecting group. The methods for the introduction of the protecting groups vary depending on their nature, but are familiar to any person skilled in the art. For example, a benzyloxycarbonyl group can be introduced by means of benzyl chloroformate.

Certain compounds of formula III can also be prepared from 4-amino-2-hydroxybutyric acid using methods which bring about in one operation cyclization and introduction of the desired protecting group. Thus, for example, 3-(trimethylsilyloxy)-2-pyrrolidinone can be prepared by reacting 4-amino-2-hydroxybutyric acid in the presence of small amounts of trimethylchlorosilane with hexamethyldisilazane or with bis(trimethylsilyl)urea or with bis(trimethylsilyl)acetamide.

Alternatively, it is also possible to prepare compounds of formula IIc from compounds of the formula

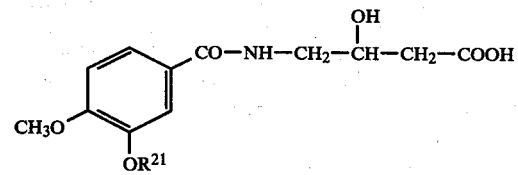

wherein $R^{21}$ is as previously described, which, in turn, can be prepared by acylating 4-amino-2-hydroxybutyric acid with a reactive derivative of an acid of formula IV, for example, with 3-benzyloxy-4-methoxybenzoyl chloride. Thus, for example, in the treatment of 4-[(3-benzyloxy-4-methoxybenzoyl)-amino]-2-hydroxybutyric acid with acetic acid anhydride there is brought about in one operation cyclization and introduction of the protecting group, that is, there is obtained a compound of formula IIc in which $R^{21}$ is benzyl and $R^{12}$ is acetyl. Examples of other reagents with which the 4-[(3-benzyloxy-4-methoxybenzoyl)amino]-2-hydroxybutyric acid or another compound of formula V can be converted in one operation into a compound of formula IIc are chloroacetic acid anhydride, methoxyacetic acid anhydride, trifluoroacetic acid anhydride, hexamethyldisilazane and the like; in the resulting compound of formula IIc $R^{22}$ is, depending on the reagent used, chloroacetyl or methoxyacetyl or trifluoroacetyl or trimethylsilyl or the like.

Furthermore, it is also possible to cyclize derivatives of compounds of formula V, the hydroxy group of which is protected, to give corresponding compounds of formula IIc; for the preparation of such derivatives of the compounds of formula V, derivatives of 4-amino-hydroxybutyric acid, the hydroxy group of which is already protected by the desired protecting group, and which can be readily prepared according to known methods are acylated at the amino group with a sufficiently reactive derivative of a compound of formula IV.

Compounds of formulas IIa and IIb can be prepared by removing one of the two protecting groups from a suitable compound of formula IIc. Thus, for example, compound E mentioned earlier, that is, formula IIc in which $R^{12}$ is acetyl and $R^{21}$ is benzyl, can be converted by hydrogenation in the presence of palladium/carbon into compound A mentioned earlier, that is, into the compound of formula IIa in which $R^{12}$ is acetyl. Furthermore, for example, compound D mentioned earlier, that is, formula IIc in which $R^{12}$ is trifluoroacetyl and $R^{21}$ is benzyl, can be converted by means of methanol into compound B mentioned earlier, that is, into the compound of formula IIb in which $R^{21}$ is benzyl. Depending upon the nature of the two protecting groups and the methods available for the cleavage of these protecting groups, it will be readily apparent to a person of ordinary skill in the art for each particular compound of formula IIc whether one of the two protecting groups can be selectively removed from it without affecting the other protecting group present therein and, in the affirmative, whether the compound of formula IIc in question can be converted into the corresponding compound of formula IIa or into the corresponding compound of formula IIb.

The compounds of formula II have an asymmetric carbon atom in the 3-position of the 5-membered heterocycle. The relevant stereochemical relationships determine the stereochemical relationships in the compound of formula I, that is, 1-(3-hydroxy-4-methoxybenzoyl)-3-hydroxy-2-pyrrolidinone, which can be prepared from the compounds of formula II. The stereochemical relationships in the 3-position of the 5-membered heterocycle of the compounds of formula II are, in turn, determined by the intermediates and/or methods used in the preparation of the compounds of formula II. It will be readily apparent to any person of ordinary skill in the art how, having regard to the relationships just described, optically active or racemic 1-(3-hydroxy-4-methoxybenzoyl)-3-hydroxy-2-pyrrolidinone can be prepared in accordance with the invention.

Thus, for example, (R)-1-(3-hydroxy-4-methoxy-benzoyl)-3-hydroxy-2-pyrrolidinone can be prepared by acylating (R)-4-amino-2-hydroxybutyric acid by means of 3-benzyloxy-4-methoxybenzoyl chloride, converting the resulting (R)-4-[(3-benzyloxy-4-methoxybenzoyl)amino]-2-hydroxybutyric acid by means of trifluoroacetic acid anhydride into (R)-1-(3-benzyloxy-4-methoxybenzoyl)-2-oxo-3-pyrrolidinyltrifluoroacetate, cleaving the trifluoroacetyl group from the latter and cleaving the benzyl group from the resulting (R)-1-(3-benzyloxy-4-methoxybenzoyl)-3-hydroxy-2-pyrrolidinone.

In an analogous manner, from (S)-4-amino-2-hydroxy-butyric acid there can be prepared (S)-1-(3-hydroxy-4-methoxybenzoyl)-3-hydroxyl-2-pyrrolidinone and from (R,S)-4-amino-2-hydroxybutyric acid there can be prepared (R,S)-1-(3-hydroxy-4-methoxybenzoyl)-3-hydroxy-2-pyrrolidinone.

As mentioned earlier, the pyrrolidine derivative of formula I is a compound which has extremely valuable pharmacodynamic properties. It exhibits only a slight toxicity and it has been shown that, in the experiment described hereinafter it is capable of counteracting cerebral insufficiency produced experimentally.

The test apparatus is a "Skinner box" with an electrifiable grid floor (30×40 cm) and a grey plastic platform (15×15×0.8 cm) in the front right corner. Untrained male rats (100–120 g) are placed individually on the platform. As soon as they climb down on to the grid floor, they receive an electric foot-shock (0.8 mA). The normal reaction of inexperienced rats is to jump back on to the platform. However, since the rats still attempt to climb down again, the foot-shock procedure must be repeated three to five times for each animal. After these three to five repetitions per animal, the rats have learned a so-called "passive avoidance response", that is, they no longer attempt to descend to the grid floor, since they know that they are punished when they do so.

Immediately thereafter three groups each comprising 30 animals are set up. The first group receives an injection intraperitoneally of 0.3 mg/kg of scopolamine as well as distilled water, 2 ml/kg orally. The second group receives an injection intraperitoneally of 0.3 mg/kg of scopolamine and an oral dosage of the test substance. The third group receives only distilled water orally.

Two (2) hours later each rat is placed once on the platform in the "Skinner box". The criterion for the assessment of this test for the determination of a preparation having activity on the short-time memory is whether the animal remains or does not remain for 60 seconds on the platform. The result can thus only read "yes" or "no" for each animal. The statistical significance of the difference between the results obtained in the first and in the second group is determined by means of the Chi-Square Test.

Of the animals treated only with distilled water orally, 70–75% still remember 2–4 hours after learning the "passive avoidance response" that they should remain on the platform. In the case of 85–92% of the animals treated with scopolamine (0.3 mg/kg intraperitoneally) and distilled water orally, there can be established during 3–4 hours a retrograde effect on the short-time memory, that is, they have forgotten that they must remain on the platform. A substance which is capable of counteracting cerebral insufficiency can reverse the blocking of the short-time memory caused by the intraperitoneal injection of 0.3 mg/kg of scopolamine. A dosage of a preparation is denoted as "active" against scopolamine if the number of positive results, that is "yes", is significantly different from those of control animals treated with scopolamine (0.3 mg/kg intraperitoneally) and only distilled water orally.

In the following Table there are compiled the dosages at which the racemate and the two optically uniform enantiomeric forms of the compound of formula I exhibit a significant activity in the test previously described. Moreover, the Table contains data concerning the acute toxicity, that is, $LD_{50}$ in mg/kg in the case of single oral administration to mice.

| Configuration | Significant active dosage | LD 50 |
| --- | --- | --- |
| R,S | 1 mg/kg p.o. (after 2 hrs.) | >5000 mg/kg p.o. |
|  | 10 mg/kg p.o. (after 2 hrs.) |  |
|  | 30 mg/kg p.o. (after 2 hrs.) |  |
|  | 50 mg/kg p.o. (after 2 hrs.) |  |
| R | 30 mg/kg p.o. (after 2 hrs.) | >5000 mg/kg p.o. |
|  | 50 mg/kg p.o. (after 2 hrs.) |  |
|  | 100 mg/kg p.o. (after 2 hrs.) |  |
| S | 30 mg/kg p.o. (after 2 hrs.) | >4000 mg/kg p.o. |
|  | 50 mg/kg p.o. (after 2 hrs.) |  |

The compound of formula I can be used as a medicament, for example, in the form of pharmaceutical compositions. The pharmaceutical compositions can be administered orally, for example, in the form of tablets, coated tablets, dragees, hard and soft gelatine capsules, solutions, emulsions or suspensions. They can, however, also be administered rectally, for example, in the form of suppositories or parenterally, for example, in the form of injections.

As mentioned earlier, medicaments containing the compound of formula I also form part of the invention as is a process for the preparation of such medicaments which comprises bringing the compound of formula I and, if desired, one or more other therapeutically valuable substances into a galenical administration form.

To prepare tablets, coated tablets, dragees and hard gelatine capsules, the compound of formula I can be processed with pharmaceutical inert, inorganic or organic excipients. As excipients for tablets, dragees and hard gelatine capsules one can use lactose, maize starch or derivatives thereof, talc, stearic acid or its salts, and the like.

Suitable excipients for soft gelatine capsules are, for example, vegetable oils, waxes, fats, semi-solid and liquid polyols and the like.

Suitable excipients for the preparation of solutions and syrups are, for example, water, polyols, saccharose, invert sugar, glucose and the like.

Suitable excipients for injection solutions, that is, injectables, are, for example, water, alcohols, polyols, glycerine, vegetable oils and the like.

Suitable excipients for suppositories are, for example, natural or hardened oils, waxes, fats, semi-liquid or liquid polyols and the like.

Moreover, the pharmaceutical compositions can contain preserving agents, solubilizing agents, stabilizing agents, wetting agents, emulsifying agents, sweetening agents, coloring agents, flavoring agents, salts for the varying of the osmotic pressure, buffers, coating agents or antioxidants. They can also contain still other therapeutically active substances.

In accordance with the invention, the compound of formula I can be used in the control or prevention of cerebral insufficiency; for example, in the case of cerebral seizures, in geriatrics, and in alcoholism. The dosage can vary within wide limits and is, of course, fitted to the individual requirements in each particular case. In general, in the case of oral administration a daily dosage of about 10 mg to 2500 mg of the compound of formula I should be appropriate, although the upper limit quoted can be exceeded when this is shown to be indicated.

The Examples which follow further illustrate the invention. In the Examples, all temperatures are given in degrees Centigrade.

EXAMPLE 1

Preparation of (R,S)-1-(3-hydroxy-4-methoxybenzoyl)-3-hydroxy-2-pyrrolidinone (a)

20.0 g of 3-benzyloxy-4-methoxybenzoyl chloride and 20 ml of tetrahydrofuran are added while stirring well to 4.3 g of (R,S)-4-amino-2-hydroxybutyric acid in 80 ml of deionized water. Thereafter, the mixture is brought to a pH of 10.5 with 2N sodium hydroxide and held at this pH for 180 minutes by adding 2N sodium hydroxide. The suspension is then filtered, whereupon the filtrate is treated with ice and its pH is adjusted to 1 with 25% hydrochloric acid. The precipitated solid material is removed by filtration, washed with water, dried and ground, whereupon 800 ml of methylene chloride are added and the mixture is heated to boiling for 1 hour. The insoluble constituent, (R,S)-4-[(3-benzyloxy-4-methoxybenzoyl)amino]-2-hydroxybutyric acid, is removed by filtration and washed with methylene chloride. By concentrating the filtrate there can be obtained additional (R,S)-4-[(3-benzyloxy-4-methoxybenzoyl)-amino]-2-hydroxybutyric acid; m.p. 140°–141°.

(b)

4.0 g of (R,S)-4-[(3-benzyloxy-4-methoxybenzoyl)-amino]-2-hydroxybutyric acid and 0.55 g of sodium trifluoroacetate are boiled at reflux while stirring in 24 ml of trifluoroacetic acid anhydride for 48 hours. After evaporating the mixture, the residue is shaken four times with toluene, and the toluene is thereafter evaporated in vacuo. The residue, containing (R,S)-1-(3-benzyloxy-4-methoxybenzoyl)-2-oxo-3-pyrrolidinyl-trifluoro acetate, is boiled at reflux in absolute methanol for 30 minutes. After evaporating the methanol, the residue is treated with ethyl acetate and water. The insoluble solid material is removed by filtration and there is obtained (R,S)-1-(3-benzyloxy-4-methoxybenzoyl)-3-hydroxy-2-pyrrolidinone of melting point 182°–183°. From the organic phase of the filtrate there can be isolated an additional amount of this product having the same melting point.

(c)

1.8 g of (R,S)-1-(3-benzyloxy-4-methoxybenzoyl)-3-hydroxy-2-pyrrolidinone are dissolved in 70 ml of tetrahydrofuran and hydrogenated over 1.5 g of 5% of palladium/carbon with hydrogen at atmospheric pressure. After removal of the catalyst by filtration and concentrating the filtrate, the residue is stirred in diethyl ether at room temperature. The solid material is removed by filtration and there is thus obtained (R,S)-1-(3-hydroxy-4-methoxybenzoyl)-3-hydroxy-2-pyrrolidinone having a melting point of 131°–132°.

EXAMPLE 2

Preparation of (R,S)-1-(3-hydroxy-4-methoxybenzoyl)-3-hydroxy-2-pyrrolidinone (a)

4.6 g of (R,S)-4-[(3-benzyloxy-4-methoxybenzoyl)amino]-2-hydroxybutyric acid are boiled at reflux in 12 ml of acetic acid anhydride for 15 minutes. After evaporating the mixture, the residue is shaken six times with toluene, and the toluene is thereafter evaporated in vacuo. There is obtained (R,S)-1-(3-benzyloxy-4-methoxybenzoyl)-2-oxo-3-pyrrolidinylacetate of melting point 140°–141°.

(b)

4.60 g of (R,S)-1-(3-benzyloxy-4-methoxybenzoyl)-2-oxo-3-pyrrolidinylacetate are hydrogenated in 100 ml of acetic acid over 2.0 g of 5% palladium/carbon with hydrogen at atmospheric pressure. After removal of the catalyst by filtration and evaporating the acetic acid in vacuo, there is obtained, after stirring up in diethyl ether, (R,S)-1-(3-hydroxy-4-methoxybenzoyl)-2-oxo-3-pyrrolidinylacetate or melting point 141°–142°.

(c)

1710 units of esterase enzyme are added to 0.50 g of ground (R,S)-1-(3-hydroxy-4-methoxybenzoyl)-2-oxo-3-pyrrolidinylacetate in 20 ml of 0.05 molar potassium sodium phosphate buffer of pH 6.61, whereupon the mixture is stirred at room temperature for 195 minutes and then the insoluble constituents are filtered off. The filtrate is stirred at room temperature for an additional 135 minutes and thereafter extracted with ethyl acetate. The ethyl acetate phase is washed with water. The aqueous phases are back-extracted with ethyl acetate. The combined ethyl acetate extracts are dried over sodium sulfate, filtered and evaporated. (R,S)-1-(3-Hydroxy-4-methoxybenzoyl)-3-hydroxy-2-pyrrolidinone can be detected in the residue by two-dimensional thin-layer chromatography.

EXAMPLE 3

Preparation of
(R,S)-1-(3-hydroxy-4-methoxybenzoyl)-3-hydroxy-2-pyrrolidinone (a)

6.0 g of (R,S)-3-hydroxy-2-pyrrolidinone are dissolved in 120 ml of pyridine, whereupon 24 ml of benzyl chloroformate are added at 0° to 5° and thereafter the mixture is stirred at room temperature for 22 hours. The mixture is evaporated, whereupon the residue is stirred in toluene and again evaporated. The residue is partitioned between ethyl acetate and water. The organic phase is washed with water and the water phases are back-extracted with ethyl acetate. The combined ethyl acetate phases are dried over sodium sulfate and evaporated. The crystalline residue is dissolved in 700 ml of dioxane at reflux temperature and left to stand at +5°; there is obtained (R,S)-3-(benzyloxycarbonyloxy)-2-pyrrolidinone of melting point 81°-82°.

(b)

5.0 g of (R,S)-3-(benzyloxycarbonyloxy)-2-pyrrolidinone are silylated in tetrahydrofuran using trimethylchlorosilane and triethylamine. There is obtained (R,S)-3-(benzyloxycarbonyloxy)-1-trimethylsilyl-2-pyrrolidinone of melting point 56°-58°.

(c)

3.30 g of (R,S)-3-(benzyloxycarbonyloxy)-1-trimethylsilyl-2-pyrrolidinone are mixed with 2.97 g of 3-benzyloxy-4-methoxybenzoyl chloride, whereupon the mixture is stirred at room temperature. Thereupon, the resulting trimethyldichlorosilane is distilled under reduced pressure in an oil-bath of 100°. The residue is partitioned between ethyl acetate and water. The organic phase is treated with active carbon, dried over sodium sulfate and evaporated. After stirring the residue in diethyl ether, there is obtained (R,S)-3-(benzyloxycarbonyloxy)-1-(3-benzyloxy-4-methoxybenzoyl)-2-pyrrolidinone of melting point 125°-126°.

(d)

3.0 g of (R,S)-3-(benzyloxycarbonyloxy)-1-(3-benzyloxy-4-methoxybenzoyl)-2-pyrrolidinone are hydrogenated in 60 ml of tetrahydrofuran over 1.5 g of 5% palladium/carbon with hydrogen at atmospheric pressure. After removal of the catalyst by filtration and concentrating the filtrate, there is obtained (R,S)-1-(3-hydroxy-4-methoxybenzoyl)-3-hydroxy-2-pyrrolidinone which melts at 125°-126° after stirring in diethyl ether.

EXAMPLE 4

Preparation of
(R)-1-(3-hydroxy-4-methoxybenzoyl)-3-hydroxy-2-pyrrolidinone (a)

20.0 g of 3-benzyloxy-4-methoxybenzoyl chloride and 20 ml of tetrahydrofuran are added while stirring well to 4.3 g of (R)-4-amino-2-hydroxybutyric acid in 80 ml of deionized water. Thereafter, the mixture is adjusted to a pH of 10.5 with 2N sodium hydroxide and held at this pH for 200 minutes by adding 2N sodium hydroxide. The suspension is then filtered, whereupon the filtrate is treated with ice and its pH is adjusted to 1.4 with 25% hydrochloric acid. The precipitated solid material is removed by filtration, washed ion-free with water, dried and chromatographed on 90 g of silica gel (granular size 0.2 to 0.5 mm). The almost pure (R)-4-[(3-benzyloxy-4-methoxybenzoyl)amino]-2-hydroxybutyric acid, which is eluted with ethyl acetate, exhibits a melting point of 138°-140° after recrystallization from acetonitrile.

(b)

5.0 g of (R)-4-[(3-benzyloxy-4-methoxybenzoyl)amino]-2-hydroxy-butyric acid and 0.70 g of sodium trifluoroacetate are boiled at reflux while stirring in 30 ml of trifluoroacetic acid anhydride for 48 hours. After evaporation of the mixture, the residue is shaken three times with toluene, and the toluene is thereafter evaporated in vacuo. The residue, containing (R)-1-(3-benzyloxy-4-methoxybenzoyl)-2-oxo-3-pyrrolidinyltrifluoroacetate, is boiled at reflux in absolute methanol for 30 minutes. After evaporation of the methanol, the residue is treated with ethyl acetate. The insoluble constituents are removed by filtration and there is obtained, after recrystallization from ethyl acetate/n-hexane, (R)-1-(3-benzyloxy-4-methoxybenzoyl)-3-hydroxy-2-pyrrolidinone of melting point 164°-166°; $[\alpha]_D^{20} = +143°$; $[\alpha]_{546}^{20} = +177°$; $[\alpha]_{365}^{20} = +866°$ (chloroform, c=1.0).

(c)

2.20 g of (R)-1-(3-benzyloxy-4-methoxybenzoyl)-3-hydroxy-2-pyrrolidinone are hydrogenated in 60 ml of tetrahydrofuran over 1.80 g of 5% palladium/carbon with hydrogen at atmospheric pressure. After removal of the catalyst by filtration, concentration of the filtrate and recrystallization of the residue from ethyl acetate/n-hexane, there is obtained (R)-1-(3-hydroxy-4-methoxybenzoyl)-3-hydroxy-2-pyrrolidinone of melting point 129°-131°; $[\alpha]_D^{20} = +175°$; $[\alpha]_{546}^{20} = +216°$; $[\alpha]_{436}^{20} = +451°$ (chloroform, c=1.0).

EXAMPLE 5

Preparation of
(S)-1-(3-hydroxy-4-methoxybenzoyl)-3-hydroxy-2-pyrrolidinone (a)

15.5 g of 3-benzyloxy-4-methoxybenzoyl chloride and 20 ml of tetrahydrofuran are added while stirring well to 5.06 g of (S)-4-amino-2-hydroxybutyric acid in 130 ml of deionized water. Thereafter, the mixture is adjusted to a pH of 10.5 with 2N sodium hydroxide and held at this pH for 180 minutes by adding 2N sodium hydroxide. The suspension is then filtered, whereupon the filtrate is treated with ice, the pH is adjusted to 1.4 with 25% hydrochloric acid and the mixture is extracted with ethyl acetate. The ethyl acetate extract is evaporated and the residue is boiled at reflux in 240 ml of methylene chloride. The insoluble (S)-4-[(3-benzyloxy-4-methoxybenzoyl)amino]-2-hydroxy-butyric acid is filtered; it melts at 138°-140° after recrystallization from acetonitrile.

(b)

6.5 g of (S)-4-[(3-benzyloxy-4-methoxybenzoyl)amino]-2-hydroxybutyric acid and 1.0 g of sodium trifluoroacetate are boiled at reflux while stirring in 40 ml of trifluoroacetic acid anhydride for 48 hours. After evaporation of the mixture, the residue is shaken three times with toluene, and the toluene is thereafter evaporated in vacuo. The residue, containing (S)-1-(3-benzyloxy-4-methoxybenzoyl)-2-oxo-3-pyrrolidinyltrifluoroacetate, is boiled at reflux in 40 ml of absolute methanol for 30 minutes. Thereafter, the mixture is stirred at room temperature for an additional 1 hour, whereupon the solid material is removed by filtration and washed with methanol. There is obtained (S)-1-(3-benzyloxy-4-methoxybenzoyl)-3-hydroxy-2-pyrrolidinone which melts at 166°–167° after recrystallization from methanol; $[\alpha]_D^{20} = -146°$; $[\alpha]_{546}^{20} = -180°$; $[\alpha]_{365}^{20} = -879°$ (chloroform, c=1.0).

(c)

2.40 g of (S)-1-(3-benzyloxy-4-methoxybenzoyl)-3-hydroxy-2-pyrrolidinone are hydrogenated in 100 ml of tetrahydrofuran over 2.00 g of 5% palladium/carbon with hydrogen at atmospheric pressure. After removal of the catalyst by filtration, concentration of the filtrate and crystallization from ethyl acetate/diethyl ether, there is obtained (S)-1-(3-hydroxy-4-methoxybenzoyl)-3-hydroxy-2-pyrrolidinone of melting point 131°–132°; $[\alpha]_D^{20} = -180°$; $[\alpha]_{546}^{20} = -223°$; $[\alpha]_{436}^{20} = -464°$ (chloroform, c=1.0).

EXAMPLE A 1-(3-Hydroxy-4-methoxybenzoyl)-3-hydroxy-2-pyrrolidinone is used as the active ingredient for the preparation of tablets of the following composition:

|  | Per tablet |
| --- | --- |
| Active ingredient (finely ground) | 25 mg |
| Lactose (powdered) | 180 mg |
| Maize starch (white) | 275 mg |
| Polyvinylpyrrolidone | 15 mg |
| Magnesium stearate | 5 mg |
|  | 500 mg |

The finely ground active ingredient, the powdered lactose and a portion of the white maize starch are mixed with one another. The mixture is sieved, moistened with a solution of polyvinylpyrrolidone in water, kneaded, moist granulated and dried. The granulate, the remainder of the maize starch and the magnesium stearate are sieved and mixed with one another. The mixture is pressed to tablets of suitable form and size.

EXAMPLE B 1-(3-Hydroxy-4-methoxybenzoyl)-3-hydroxy-2-pyrrolidinone is used as the active ingredient for the preparation of tablets of the following composition:

|  | Per tablet |
| --- | --- |
| Active ingredient (finely ground) | 20 mg |
| Maize starch (white) | 220 mg |
| Lactose | 70 mg |
| Microcrystalline cellulose | 40 mg |
| Polyvinylpyrrolidone | 20 mg |
| Sodium carboxymethylstarch | 23 mg |
| Magnesium stearate | 2 mg |
|  | 395 mg |

The finely ground active ingredient, a portion of the white maize starch, the lactose, the microcrystalline cellulose and the polyvinylpyrrolidone are mixed with one another. The mixture is sieved and processed with the remainder of the white maize starch and water to give a granulate which is dried and sieved. Then, the sodium carboxymethylstarch and the magnesium stearate are added thereto, mixed and the mixture is pressed to tablets of suitable size, which have a break-bar.

EXAMPLE C 1-(3-Hydroxy-4-methoxybenzoyl)-3-hydroxy-2-pyrrolidinone is used as the active ingredient for the preparation of tablets of the following composition:

|  | Per tablet |
| --- | --- |
| Active ingredient (finely ground) | 125 mg |
| Maize starch (white) | 560 mg |
| Lactose | 165 mg |
| Microcrystalline cellulose | 70 mg |
| Polyvinylpyrrolidone | 35 mg |
| Sodium carboxymethylstarch | 40 mg |
| Magnesium stearate | 5 mg |
|  | 1000 mg |

The finely ground active ingredient, a portion of the white maize starch, the lactose, the microcrystalline cellulose and the polyvinylpyrrolidone are mixed with one another. The mixture is sieved and processed with the remainder of the white maize starch and water to give a granulate which is dried and sieved. Then, the sodium carboxymethylstarch and the magnesium stearate are added thereto, mixed and the mixture is pressed to tablets of suitable size, which have a break-bar.

EXAMPLE D 1-(3-Hydroxy-4-methoxybenzoyl)-3-hydroxy-2-pyrrolidinone is used as the active ingredient for the preparation of duplex ampules of the following composition:

| Active ingredient solution | |
| --- | --- |
| Active ingredient | 25 mg |
| Polyethyleneglycol ad | 5 mg |
| Diluent | |
| Water for injection | 5 ml |

Prior to injection, the diluent is added to the content of the active ingredient ampule. There are obtained 10 ml of a ready-for-use injection solution containing 25 mg of active ingredient.

EXAMPLE E 1-(3-Hydroxy-4-methoxybenzoyl)-3-hydroxy-2-pyrrolidinone is used as the active ingredient for the preparation of duplex ampules of the following composition:

| Active ingredient solution | |
| --- | --- |
| Active ingredient | 25 mg |
| Glycofurol ad | 3.5 ml |
| Diluent | |
| Sodium chloride | 67.5 mg |
| Water for injection ad | 6.5 ml |

Prior to injection, the diluent is added to the content of the active ingredient ampule. There are obtained 10 ml of a ready-for-use injection solution containing 25 mg of active ingredient.

EXAMPLE F 1-(3-Hydroxy-4-methoxybenzoyl)-3-hydroxy-2-pyrrolidinone is used as the active ingredient for the preparation of duplex ampules of the following composition:

| Active ingredient solution | |
|---|---|
| Active ingredient | 25 mg |
| Polyethyleneglycol | 1.5 ml |
| Glycofurol ad | 4 ml |
| Diluent | |
| Water for injection | 6 ml |

Prior to injection, the diluent is added to the content of the active ingredient ampule. There are obtained 10 ml of a ready-for-use injection solution containing 25 mg of active ingredient.

We claim:

1. A compound, (R,S)-1-(3-hydroxy-4-methoxybenzoyl)-3-hydroxy-2-pyrrolidinone of the formula

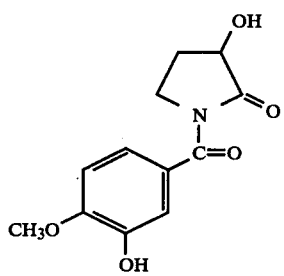

or its (R) or (S) enantiomer.

2. A compound in accordance with claim 1, (R,S)-1-(3-hydroxy-4-methoxybenzoyl)-3-hydroxy -2-pyrrolidinone.

3. A compound in accordance with claim 1, (R)-1-(3-hydroxy-4-methoxybenzoyl)-3-hydroxy -2-pyrrolidinone.

4. A compound in accordance with claim 1, (S)-1-(3-hydroxy 4-methoxybenzoyl)-3-hydroxy-2-pyrrolidinone.

5. A compound of the formula

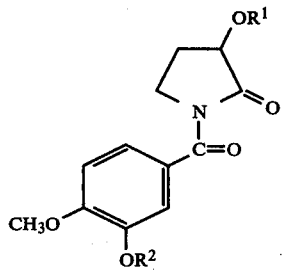

wherein $R^1$ is hydrogen, p-methoxytrityl, p,p'-dimethoxytrityl, p,p',p"-trimethoxytrityl, trimethylsilyl, tetrahydropyran-2-yl, 4-methoxytetrahydropyran-4-yl, acetyl, chloroacetyl, trifluoroacetyl, methoxyacetyl, phenoxyacetyl, benzyloxycarbonyl, trichloroethoxycarbonyl, tribromoethoxycarbonyl and benzoylformyl and $R^2$ is hydrogen, tert. butyl, benzyl, trimethylsilyl, tetrahydropyran-2-yl, fluorenecarbonyl, benzyloxycarbonyl, trichloroethoxycarbonyl and tribromoethoxycarbonyl; provided that least one of $R^1$ or $R^2$ is other than hydrogen.

6. A pharmaceutical composition for controlling or preventing cerebral insufficiency, comprising (R,S)-1-(3-hydroxy-4-methoxybenzoyl)-3 -hydroxy-2-pyrrolidinone or its (R) or (S) enantiomer, and an inert carrier.

7. A method of controlling or preventing cerebral insufficiency which comprises administering to a host requiring such treatment an effective amount of (R,S)-1-(3-hydroxy-4-methoxybenzoyl)-3-hydroxy-2-pyrrolidinone or its (R) or (S) enantiomer.

* * * * *